Figure 1:
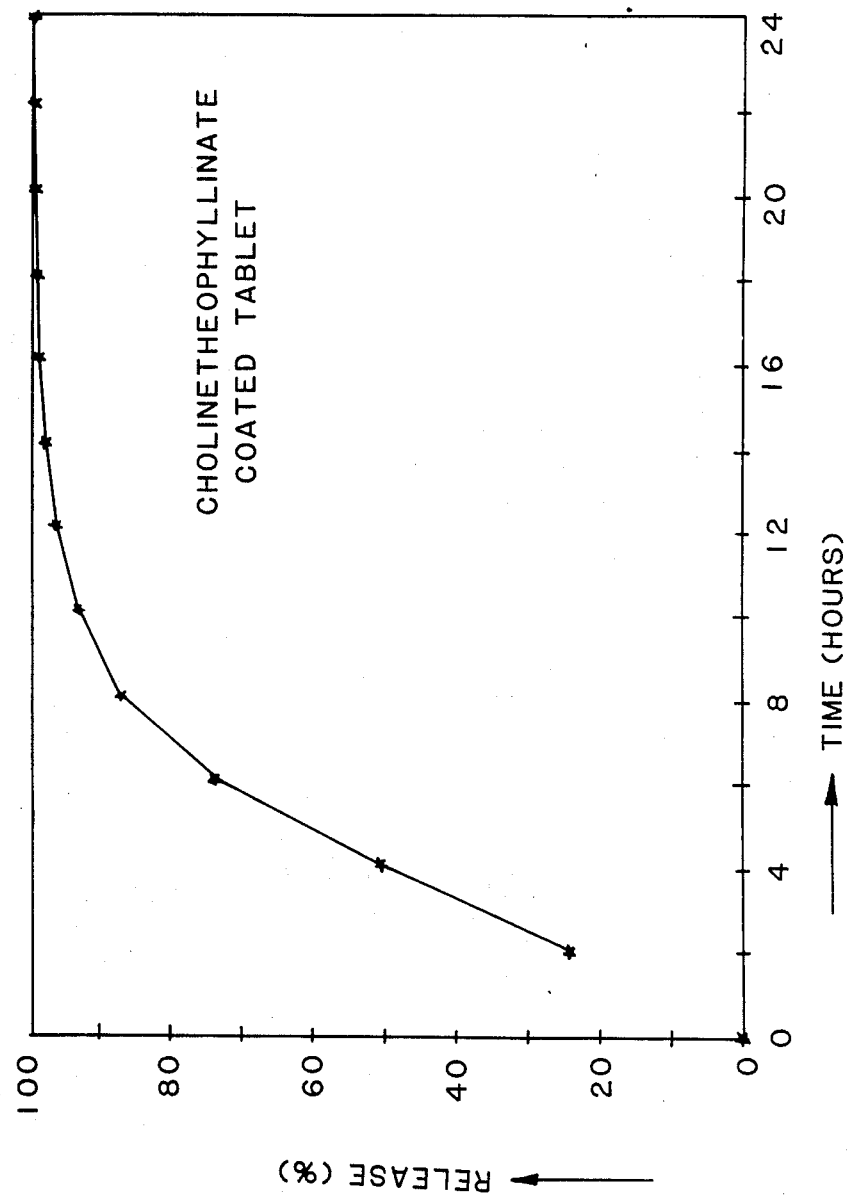

United States Patent [19]

Junginger

[11] Patent Number: 4,666,702
[45] Date of Patent: May 19, 1987

[54] DOSAGE UNITS FOR CONTROLLED RELEASE OF ACTIVE MATERIAL

[75] Inventor: Hans E. Junginger, Rijnsburg, Netherlands

[73] Assignee: Thiemann Arzneimittel GmbH, Waltrop, Fed. Rep. of Germany

[21] Appl. No.: 722,077

[22] Filed: Apr. 11, 1985

[30] Foreign Application Priority Data

Apr. 11, 1984 [EP] European Pat. Off. .......... 84.200510

[51] Int. Cl.$^4$ ........................... A61K 9/24; A61K 9/28
[52] U.S. Cl. ...................................... 424/497; 424/473
[58] Field of Search ................................. 424/19–22, 424/32, 33, 15

[56] References Cited

U.S. PATENT DOCUMENTS

| | | | |
|---|---|---|---|
| 3,096,248 | 7/1963 | Rudzki | 424/33 |
| 3,317,394 | 5/1967 | Fryklof et al. | 167/82 |
| 3,538,214 | 11/1970 | Polli et al. | 424/21 |
| 3,887,699 | 6/1975 | Yolles | 424/22 |
| 3,991,766 | 11/1976 | Schmitt et al. | 424/22 |
| 4,060,598 | 11/1977 | Groppenbacher et al. | 424/33 |
| 4,218,433 | 8/1980 | Kooichi et al. | 424/15 |
| 4,252,786 | 2/1981 | Weiss et al. | 424/21 |
| 4,428,926 | 1/1984 | Keith | 424/21 |
| 4,450,150 | 5/1984 | Sidman | 424/15 |
| 4,491,575 | 1/1985 | Kursatko | 424/21 |
| 4,525,340 | 6/1985 | Lange et al. | 424/21 |
| 4,552,752 | 11/1985 | Amick | 424/15 |

OTHER PUBLICATIONS

Chemical Abstracts, vol. 80, No. 22, Jun. 3, 1974, p. 257.
Chemical Abstracts, vol. 85, No. 18, Nov. 1, 1976, p. 451.

*Primary Examiner*—Shep K. Rose
*Attorney, Agent, or Firm*—William M. Blackstone

[57] ABSTRACT

A drug delivery system in the form of dosage units for controlled release of active material comprising a core and a coating layer enclosing said core.

The coating material contains a microporous synthetic thermoplastic polymer and is compressed into a suitable coating layer enclosing the core with the aid of relatively low compression forces.

20 Claims, 4 Drawing Figures

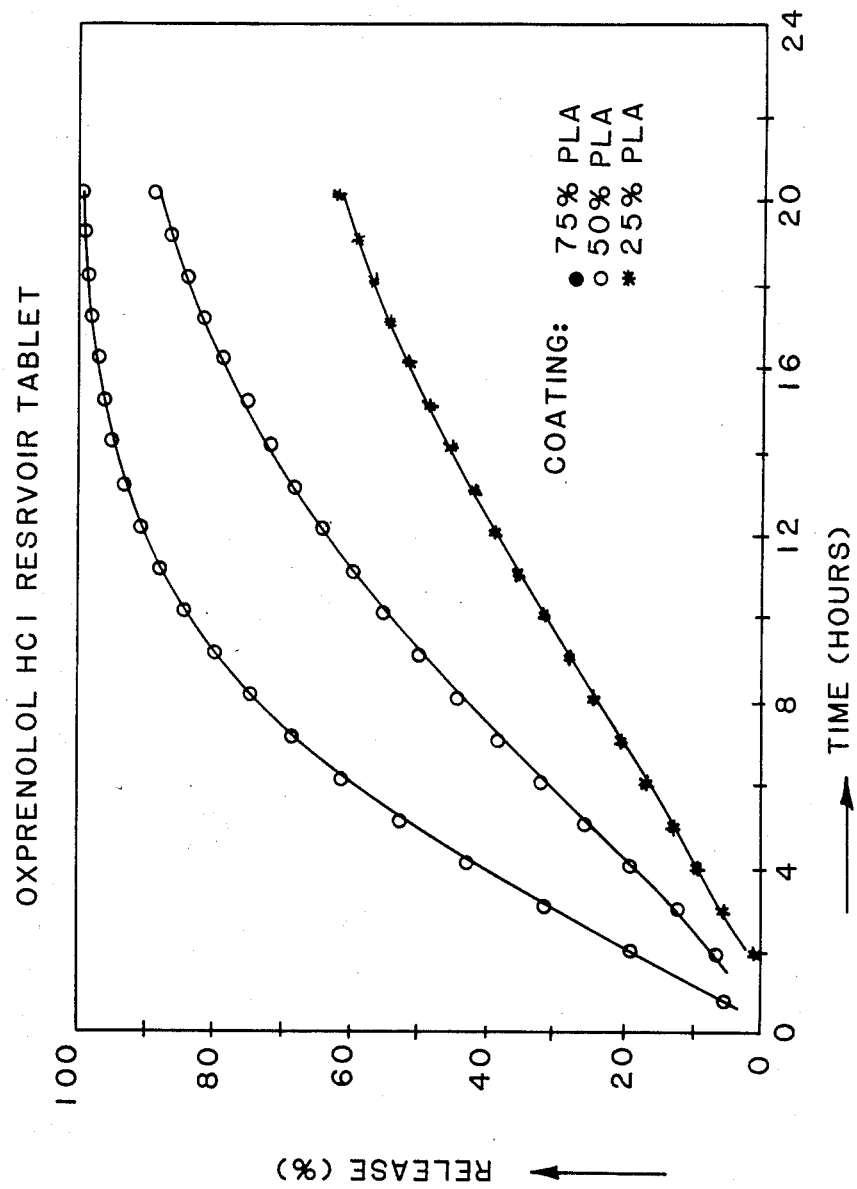

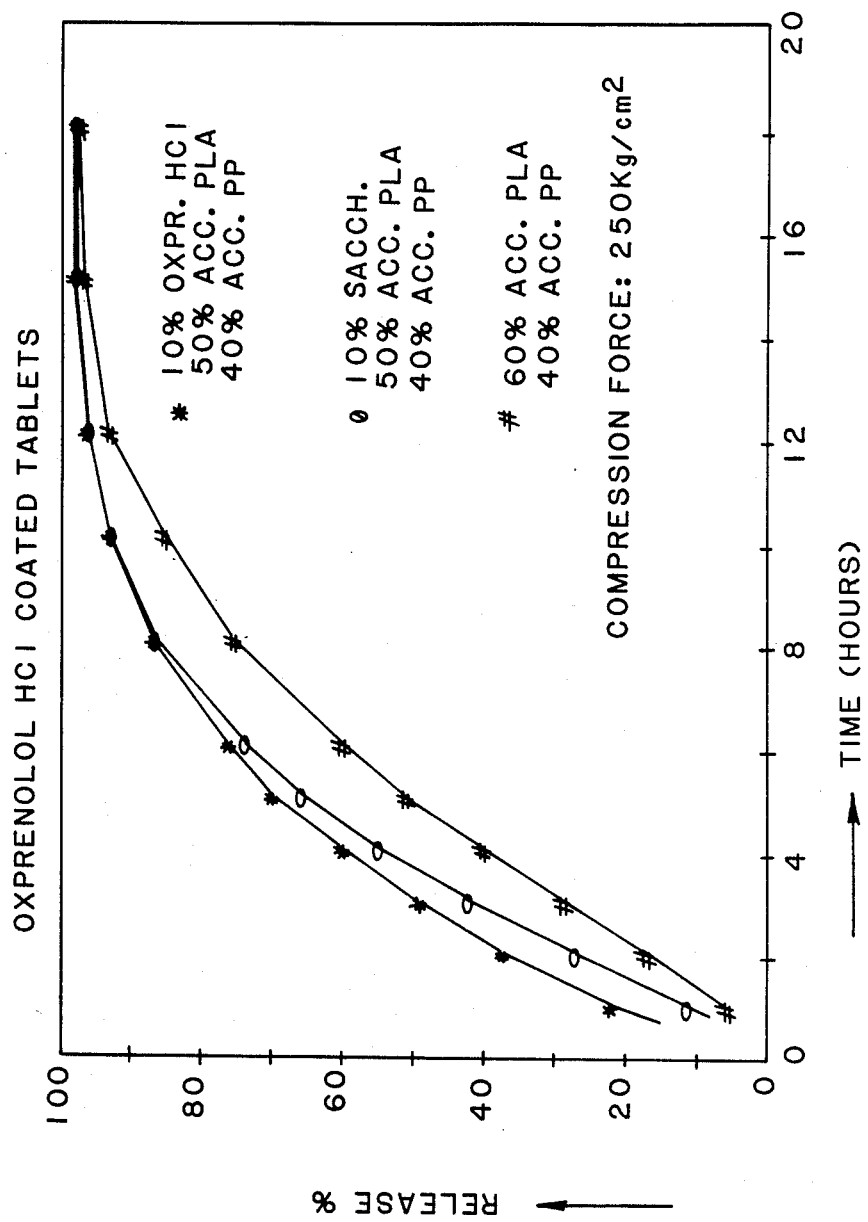

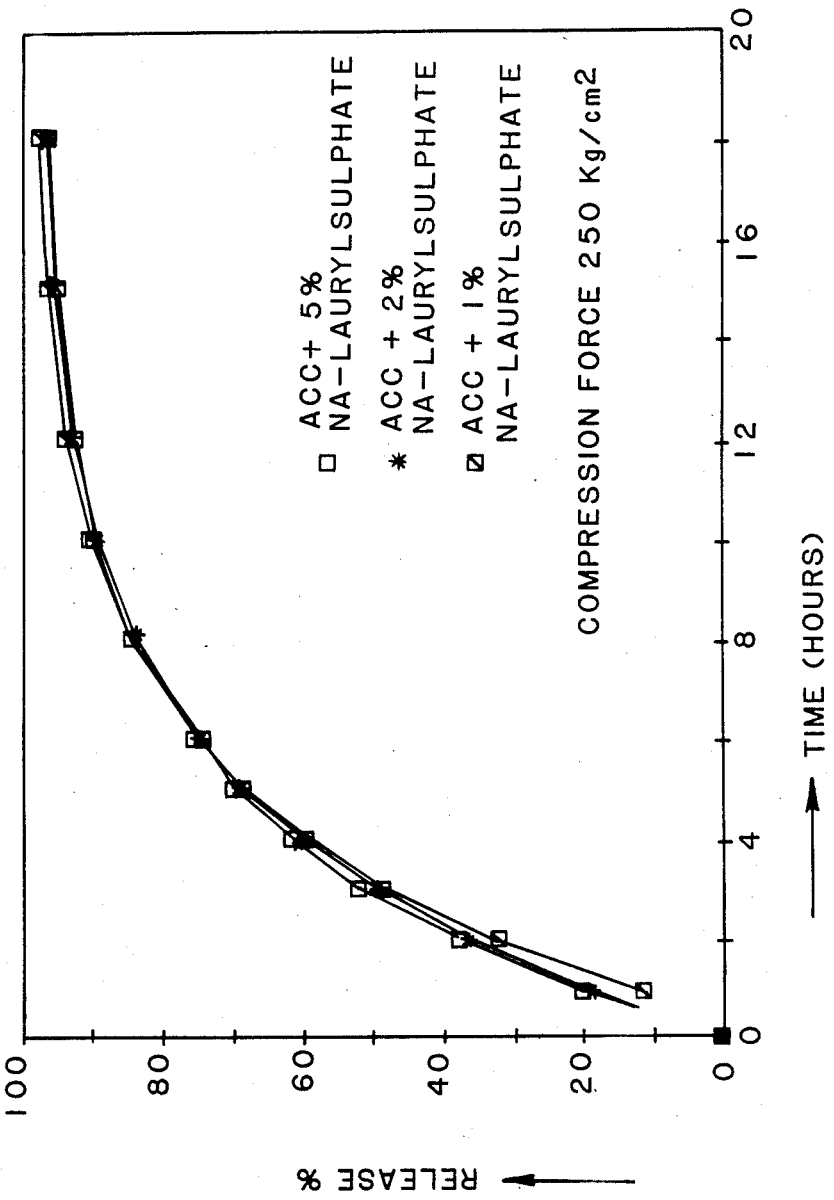

DOSAGE UNITS FOR CONTROLLED RELEASE OF ACTIVE MATERIAL

The present invention is dealing with a dosage unit for the controlled release of an active material.

Oral or parenteral administration of a biologically active substance to human beings or animals often gives rise to very irregular concentrations of the drug in the blood, especially in those cases where the drug is very rapidly metabolized in the body. Immediately after the drug's administration, its concentration in the blood will increase within a very short period, whereas—depending on the half life value of the drug—its concentration in the blood will continuously decrease after some time in such a manner that it eventually decreases below its therapeutically active level.

If therefore a more or less constant level of the drug in the blood is desired, conventional oral or parenteral administration of the drug must be repeated several times a day. The disadvantages of such frequent administration are obvious, not only from a view point of patients discomfort but also from medical point of view, since such frequent administration may result in an unnecessarily high drug concentration in the blood or even in an overdosage of the drug.

Several ideas and proposals have already been made and described in the literature to come to a controlled release system which allows a more or less constant (drug) release from the system over a longer period of time, e.g. from about one day up to several months and even one to two years, without the necessity of affecting the patient's mobility by hospitalisation or otherwise.

The controlled release systems known so far can roughly be divided into certain areas based on their mode of operation, viz. diffusion controlled systems, chemically controlled systems and systems based on osmotic pressure or other driving forces such as swelling force.

A great number of controlled release systems are based on the use of osmotic pressure, the so-called osmotic pumps. In one of these systems, which is described here by way of example, the device consists of a flexible drug-containing reservoir at least partly surrounded by a semi-permeable membrane. A saturated salt solution is present in between the flexible reservoir and the semi-permeable membrane. By diffusion of water or another external fluid through the semipermeable membrane an osmotic pressure gradient is exhibited against the reservoir forcing the drug to dispense from the device through an artificial passage-way in the said reservoir.

Other osmotic pump delivery systems consist of a tablet core containing a drug and a highly soluble salt, e.g. potassiumbicarbonate. This tablet core is coated with a water permeable membrane wherein a passage-way is placed to allow drug and salt to escape. (see for example U.S. Pat. No. 3,916,899). An example of a drug delivery system mainly based on swelling as driving force has been described in U.S. Pat. No. 4,235,236.

In the early seventies the company Alza published some release systems based on diffusion. These systems consist of a solid polymer core or a liquid core containing the drug, the core being enclosed by an outer wall or membrane that is formed of a drug release rate controlling material permeable to passage of the drug by diffusion. See for example the British Pat. Nos. 1,333,576 and 1,414,812.

Although many of these systems may release the drug according to almost zero order kinetics over a longer period of time, the manufacture procedures of these systems are complicated and require the use of sophisticated production techniques; thus they are relatively expensive.

Perhaps somewhat less complicated systems can be found amongst the coated tablets whereby the drug is coated by a variety of coating layers. An elegant method to obtain such drug delivery system consists of the coating of the drug core with a mixture of a water-soluble material and a water-insoluble polymer. In use the water-soluble material will be dissolved by the bodyfluid, thus forming pores in the coating layer which allow the drug to dispense. Examples of such coated tablets are disclosed in the U.S. Pat. Nos. 3,935,326 and 4,060,598. In practice, however, problems regarding the use of organic solvents and/or the manufacture of suitable dispersions render the coating process more difficult than could be expected. Moreover, a rapid aging of the conventional coating layer often renders the tablet suitable only for a limited period of time.

The present invention describes a delivery system in the form of dosage units that dispenses the active material according to zero order kinetics and is characterised by a very easy and thus rather economical way of manufacture. These dosage units can be prepared using conventional techniques and do not necessitate special apparatus and/or investments.

The dosage units according to the present invention comprise:

(a) a core containing the active material and
(b) a coating layer enclosing or covering said core and being comprised of one or more synthetic thermoplastic polymers, at least 50% of which being a microporous polymer, said coating layer being obtained by conventional compression forces.

Preferably the said coating layer is comprised of at least 75% by weight and more preferably 90–100% by weight of a microporous synthetic thermoplastic polymer.

Although the thickness of the coating layer is not so critical, a thicker coating layer will usually delay the start of the release of the active material considerably. A coating layer as thin as possible is therefore preferred, especially where the delivery system of the invention is used for the controlled release of a biologically active material in human beings or animals. A preferred pharmaceutical dosage unit according to the present invention and suitable for oral administration has a coating layer, the thickness of which varies between 100 and 600 $\mu$m, and more preferably between 250 and 500 $\mu$m.

It is surprising, indeed, that such relatively thin coating layer according to the invention can already be obtained by simply applying low compression forces and without the need for application of solvents, binders, external heat or other means for joining particles together.

The start of the release of the active material from the delivery system according to the invention can be influenced by increasing or decreasing the quantity of the microporous polymer in the coating layer, by increasing or decreasing the thickness of the coating layer, and/or by selecting a more hydrophylic or more hydrophobic microporous polymer in the coating layer.

Especially, where a hydrophobic microporous polymer is used in the coating layer, the start of the release of the active material can be accelerated by incorporating a wetting agent in the coating layer according to the invention.

Said wetting agent may be either present within the microporous polymer or incorporated in the coating layer by compressing a homogeneous blend of the wetting agent, the microporous polymer and optional other ingredients.

A wetting agent in the framework of this invention is not only any compound which effectiveness is related to its capacity for reducing surface tension or interfacial tension, but includes any compound which is well soluble in water. Obviously the wetting agent to be used in a pharmaceutical delivery system according to the invention should be therapeutically and pharmaceutically acceptable.

Examples of wetting agents to be used in nonpharmaceutical delivery systems according to this invention are e.g. soaps, detergents, any surface active agent and various water-soluble compounds such as salts, sugars etc. Examples of wetting agents which can be used in the pharmaceutical dosage units according to the invention are pharmaceutically acceptable surface active agents (such as sodiumlaurylsulphate, dodecyltrimethylammoniumbromide, polysorbates, etc.), water-soluble sugars (such as glucose, fructose, lactose, saccharose, sucrose, etc.), pharmaceutically acceptable salts (such as NaCl, sodiumphosphate, sodiumglutamate, sodiumgluconate etc.), water-soluble acids including amino acids, such as citric acid, glycine, alanine, glutamine, lysine etc. and other water soluble compounds, such as polyethyleneglycol preferably having a mol. weight above 3000.

In a preferred embodiment of the present invention the wetting agent may also be selected from the material to be used as (biologically) active material provided the material in question is well soluble in water. In such preferred embodiment the active material being present (as wetting agent) in the coating layer does not have the function of an initial dose—as for example in a conventional coated tablet—but does only accelerate the start of the (zero order) release of the active material.

The quantity of the wetting agent in the coating is not particularly critical, but a quantity that is necessary for the formation of additional pores from the outside through the coating layer has to be avoided. The minimum quantity for such additional pores depends on the specific gravity of the materials used but is generally not below 5-10% of the total coating material and usually much higher. The amount of wetting agent should therefore less than about 10% and preferably less than 5% of the total coating material.

The microporous polymer needed in the coating layer is a synthetic thermoplastic polymer in the form of particles containing cells which are accessible from the outside and having a total void volume from about 20 up to 95 percent (vol.). One of the preferred porous polymers has a structure of pores and cells, in which the cells have an average diameter of 0.1-100 $\mu$m and the pores have an average diameter being smaller than that of the cells. A very useful porous polymer possesses a void volume between 30 and 90% (vol.) and more preferably between 60 and 90% (vol.) and has cells with an average diameter of 1-25 $\mu$m and pores with a diameter being 2-200 times smaller than that of the cells.

The synthetic thermoplastic polymers to be used in the coating layer and being either porous or non-porous may be selected from any homopolymer, copolymer or mixture of various homopolymers and/or copolymers provided they are in the form of particles. In general, the preferred synthetic thermoplastic polymers are condensation polymers, such as nylon, polylactic acid, polyglycolic acid and copolymers thereof, oxidation polymers, such as polyphenylene oxide, and especially olefinic polymers, such as polyethylene, polypropylene, polystyrene, polyvinylchloride, polymethylacrylate, polymethylmethacrylate and ethyleneacrylic acid copolymers.

The particle size of the porous and optional non-porous polymers to be used in the coating layer is not critical but varies, in general, between 25 and 200 $\mu$m.

The porous polymers can be prepared by any conventional process which results in a polymer that meets the above requirements. Suitable porous polymers are, for example, described in the U.S. Pat. Nos. 3,969,483 and 4,247,498 and in the European patent applications Nos. 44,051 and 44,052. A very suitable polymer is sold under the tradename Accurel P.P., a porous polymer from polypropylene.

The non-porous particles may be obtained by simple grinding of a solid resin of any physical form.

The delivery system according to the invention possesses a core containing the active material, which core functions as a reservoir for the active material and is enclosed or covered by the said coating layer.

Besides the active material the core may contain other ingredients such as binders, fillers, lubricants etc.

The active material may, however, also be included in a suitable polymer, e.g. in the form of a matrix system or absorbed on to the polymer. Useful polymers for this purpose may be selected from the porous or non-porous synthetic thermoplastic polymers described before as ingredients of the coating material, whereby the porous polymers are to be preferred.

Preferably the core is obtained by physically combining the active material and the optional other ingredients in a conventional manner, followed if necessary by granulation of the mixture or blend, and subjecting the blend obtained to an effective pressure in order to produce the desired shape of the core (tablet, disc. grain, sphere, sheet etc.).

In an analogous manner a core, in which the active material has been incorporated in a polymer (preferably a microporous polymer) is obtained by combining the active material and the plurality of polymeric particles to produce a dry blend and subjecting the blend to an effective pressure in order to produce the desired shape of the core (tablet, disc, grain, sphere, sheet, etc.).

The diameter of the core or the thickness of the core layer is substantially determined by the quantity of the active material that is needed to provide a zero order release over the desired period of time.

The release from the delivery system according to the invention takes place according to zero order kinetics as long as the core can provide and maintain a saturated solution of the active material.

The compressional forces needed in the preparation of the coating layer are within wide limits in agreement with the compressional forces usually applied in the preparation of conventional solid dosage units. They are, however, much lower than the compressional forces needed for compressing non-porous polymer powders.

A significant and suitable strength will be obtained by applying a pressure within the range of from 25 up to about 750 kg per cm² and more preferably from 100–500 kg/cm².

A pressure which substantially exceeds about 750 kg per cm² forces the microporous polymer to completely collapse, which means that the original microporous structure has fully disappeared.

In a preferred embodiment of the invention the core material consisting essentially of a blend of the active material and optional binder(s), filler(s) and lubricant(s) is compressed to tablets, whereupon these tablets are coated by compressing the afore defined coating material on to the surface of the tablets. These coated tablets are very suitable to be applied as oral pharmaceutical dosage units.

In another embodiment of the invention the core material consisting essentially of a blend of the active material and optional binder(s), filler(s) and lubricant(s) is compressed to tablets and then grinded to particles of the desired size or is extruded into segments of the desired size. The granules, particles or segments are subsequently mixed with the afore defined coating material and then compressed by means of a rolling machine resulting in an inhomogenous film that can easily be grinded to produce coated particles.

These coated particles, contained in capsules, are particularly suitable as an oral preparation, if a high local concentration of the active material in the stomach or intestines is to be avoided.

In another preferred embodiment of the invention the core material consisting essentially of a blend of active material, a synthetic thermoplastic microporous polymer and optionally a non porous polymer and/or a binder, is compressed and rolled out into a homogeneous sheet or film by means of a rolling machine.

The above defined coating material is also compressed and rolled out by a rolling machine to form a thin sheet or film of the coating material. Subsequently the sheet of core material is provided either
- at both sides with a sheet of the coating material, or
- only at one side with a sheet of coating material and at the other side with a closing layer which is inert and does not allow any transport of active material. Suitable dosage units may be cut out or punched from this two or three layer system. This embodiment of the invention may, for example, be applied in the manufacture of a transdermal delivery system.

The active material to which this invention refers is preferably solid at room temperature. The active material may be active in any sense of the word, that is to say they may be flavors, parfums, pesticides or the like. Preferably, however, the active material is a biologically active agent (or drug), which means that the invention can most preferably be used in the preparation of pharmaceutically acceptable dosage unit forms.

EXAMPLE 1

Coated tablet

Cholin-theophyllinate and colloidal silicon-dioxide were mixed for about 10 minutes after which magnesium stearate (lubricant) was added while mixing. The mixture was compressed to tablets of about 260 mg consisting of:

| | |
|---|---|
| Cholin-theophyllinate | 98.75% by weight |
| colloidal silicondioxide | 0.25% by weight |
| magnesium stearate | 1.00% by weight |

The core-tablet, weight 260 mg, was mixed with microporous polypropylene having a void space of 75% (Accurel P.P.) and compressed into a coated tablet having a total weight of 360 mg and an average thickness of the coating layer of 450 μm (compression force of 300 kg per cm²).

This tablet started to release the active material at a constant rate about 4 hours after oral administration.

EXAMPLE 2

Coated tablet

The same core tablet as prepared in Example 1, weight 260 mg, was mixed with a blend consisting of (on weight basis):

| | |
|---|---|
| porous polylactic acid (void space 60%) | 45% |
| porous polypropylene (void space 75%) | 44% |
| polyethylene glycol (mol. weight 6000) | 10% |
| magnesium stearate | 0.5% |
| colloidal silicondioxide | 0.5% | are then compressed into a coated tablet having a total weight of 360 mg and an average thickness of the coating layer of 450 μm (release: see FIG. 1). Compression force 250 kg/cm².

EXAMPLE 3

Matrix tablet (for comparative purposes)

Oxprenolol hydrochloride was blended with aerosil, after which polyethylene glycol 6000, porous polypropylene (Accurel P.P.) and magnesiumstearate were added. This blend was compressed into tablets without previous granulation.

The matrix tablet thus prepared consists of

| | |
|---|---|
| oxprenolol.HCl | 45% (by weight) |
| polyethylene glycol 6000 | 5% |
| porous polypropylene (void space 70–75%) | 49% |
| colloidal silicondioxide (aerosil) | 0.5% |
| magnesiumstearate | 0.5% |

The particle size of all ingredients used was ≦200 μm. The tablet obtained had a diameter of 11.5 mm and a total weight of 175 mg.

This tablet, which was prepared for comparative purposes, released 90% of the active material within the first 4 hours after administration.

EXAMPLE 4

Coated matrix tablet

The matrix tablet of Example 3, weight 175 mg, was mixed with:
(1) a blend of 25% porous polylactic acid (void space 60%, particle size 200 μm) and 75% porous polypropylene (void space 75%, particle size 100–200 μm);
(2) a blend of the same material as described in (1), but in a ratio of 50% polylactic acid and 50% polypropylene, and (3) a blend of the same material as described in (1) but in a ratio of 75% polylactic acid and 25% polypropylene, and then compressed to coated tablets having a total weight of 325 mg and an average thickness of the layer of 350 µm. Compression force 300 kg/cm².

The release characteristics of the three types of coated tablets are shown in FIG. 2.

EXAMPLE 5

| Coated matrix tablets | |
|---|---|
| Coating material A is consisting of: | |
| oxprenolol.HCl (≦200 µm) | 10% |
| porous polylactic acid | 50% |
| (void space 37%, particle size ≦200 µm) | |
| and porous polypropylene | 40% |
| (void space 70%, particle size 100-200 µm) | |
| Coating material B is consisting of: | |
| saccharose (≦200 µm) | 10% |
| porous polylactic acid | 50% |
| (void space 37%, particle size ≦200 µm), and | |
| porous polypropylene | 40% |
| (void space 70%, particle size 100-200 µm) | |
| Coating material C is consisting of: | |
| porous polylactic acid | 60% |
| (void space 37%, particle size ≦200 µm) and | |
| porous polypropylene | 40% |
| (void space 70%, particle size 100-200 µm). | |

Each coating material (A, B and C) was blended and coated around the matrix tablet of example 3 (matrix tablet oxprenolol) with a compression force of 250 kg per cm² giving tablets of total 325 mg and an average thickness of the layer of 350 µm (see FIG. 3).

EXAMPLE 6

Coated matrix tablet:

Microporous polypropylene (void space 70%, 100-200 µm) was pretreated under vacuum with sodiumlaurylsulphate in an alcoholic solution, dried and sieved through a 200 µm pore sieve. The microporous polymer then contained 1, 2 or 5% of the surfactant. This polymer was compressed with 250 kg per cm² around a matrix tablet of example 3 without further additives giving a total weight of 325 mg. The release characteristics are shown in FIG. 4.

EXAMPLE 7

Coated tablet

Antipyrine (particle size ≦200 µm) was compressed to tablets with a diameter of 9 mm. The tablets (thus containing 100% antipyrine) have an average weight of 250 mg.

Porous polypropylene (particle size 100-200 µm, void space 75%) was compressed around the above antipyrine core tablet resulting in a coated tablet having a total weight of 450 mg and an average thickness of the coating layer of 500 µm. Compression force 350 kg/cm².

I claim:

1. A substantially zero order delivery system in the form of dosage units comprising:
   (a) a core comprising at least one active material and
   (b) a relatively thin, 100 to 600 millimicron thick coating layer enclosing or covering said core comprising compression bonded particles having a particle size between about 25 and about 200 millimicrons of one or more synthetic thermopolastic polymers, at least 50% of which are microporous polymers in the form of particles having open cells therein having an average diameter of 0.1 to 100 millimicrons, with pores having an average diameter smaller than that of the cells, said microporous particles having a total void volume of from about 20% to about 95% by volume, said polymer particulates being formed into the coating layer by conventional compression pressure within the range of from 25 to about 750 Kg. Cm 2.

2. A delivery system according to claim 1 in which the said coating layer is comprised of at least 75% by weight of at least one microporous synthetic thermoplastic polymer and has a thickness varying between 100 and 600 µm.

3. A delivery system according to claim 1 characterized in that the coating layer is obtained by applying compressional forces not exceeding about 750 kg/cm².

4. A delivery system according to claim 1, in which the said coating layer contains a wetting agent in a quantity sufficient to accelerate the release of active material but not in amounts great enough to cause the formation of additional pores in the coating layer through the dissolution of materials in said coating layer and in no case exceeding 10% by weight of the total coating material.

5. A delivery system according to claim 4, in which the wetting agent in the coating layer comprises the same active material, as present in the core, said active material being highly soluble in water.

6. A delivery system according to claim 1 characterized in that the synthetic thermoplastic microporous polymer is selected from polyethylene, polypropylene, polylactic acid, polyglycolic acid, copolymer from polylactic acid and polyglycolic acid, and mixtures thereof.

7. A delivery system according to claim 1, in which the active material is a biologically active substance.

8. A drug delivery system according to claim 7 in the form of a tablet.

9. A drug delivery system according to claim 7 in the form of multiple coated particles contained in a capsule.

10. The delivery system of claim 2, wherein the coating layer is obtained by applying a compressional force not exceeding about 750 kg/cm².

11. The delivery system of claim 10, wherein said compressional force is between 100 and 500 kg/cm².

12. The delivery system of claim 2, wherein said coating layer contains a wetting agent in a quantity sufficient to accelerate the release of active material but not in amounts great enough to cause the formation of additional pores in the coating layer through the dissolution of materials in said coating layer and in no case exceeding 10% by weight of the total coating material.

13. The delivery system of claim 3, wherein said coating layer contains a wetting agent in a quantity sufficient to accelerate the release of active material but not in amount great enough to cause the formation of additional pores in the coating layer through the dissolution of materials in said coating layer and in no case exceeding 10% by weight of the total coating material.

14. The delivery system of claim 2 wherein said synthetic thermoplastic microporous polymer is selected from the group consisting of polyethylene, polypropylene, polylactic acid, polyglycolic acid, a copolymer of polylactic acid and polygly colic acid, and mixtures thereof.

15. The delivery system of claim 3 wherein said synthetic thermoplastic microporous polymer is selected from the group consisting of polyethylene, polypropylene, polylactic acid, polyglycolic acid, a copolymer of polylactic acid and polyglycolic acid, and mixtures thereof.

16. The delivery system of claim 4 wherein said synthetic thermoplastic microporous polymer is selected from the group consisting of polyethylene, polypropylene, polylactic acid, polyglycolic acid, a copolymer of polylactic acid and polyglycolic acid, and mixtures thereof.

17. The delivery system of claim 5 wherein said synthetic thermoplastic microporous polymer is selected from the group consisting of polyethylene, polypropylene, polylactic acid, polyglycolic acid, a copolymer of polylactic acid and polyglycolic acid, and mixtures thereof.

18. The delivery system of claim 2, wherein said coating layer is comprised of 90–100% by weight of at least one microporous synthetic thermoplastic polymer and has a thickness varying between 250 and 500 $\mu$m, and wherein said coating layer is obtained by applying compressional forces of between 100 and 500 kg/cm$^2$.

19. The delivery system of claim 1, characterized in that the synthetic thermoplastic polymer particulates comprise one or more homopolymers, compolymers or mixtures thereof selected from among condensation polymers, oxidation polymers and olefinic polymers.

20. The delivery system of claim 19, characterized in that the synthetic thermoplastic polymer particulates comprise one or more homopolymers, copolymers or mixtures thereof selected from among nylon, polylactic acid, polyglycolic acid, polyphenylene oxide, polyethylene, polypropylene, polyvinylchloride, polymethylacrylate, polymethylmethacrylate and ethylene-acrylic acid.

* * * * *